United States Patent
Mogul

(10) Patent No.: US 10,252,056 B2
(45) Date of Patent: Apr. 9, 2019

(54) METHOD AND APPARATUS FOR PREVENTING OR TERMINATING EPILEPTIC SEIZURES

(71) Applicant: David J. Mogul, Winnetka, IL (US)

(72) Inventor: David J. Mogul, Winnetka, IL (US)

(*) Notice: Subject to any disclaimer, the term of this patent is extended or adjusted under 35 U.S.C. 154(b) by 48 days.

(21) Appl. No.: 15/355,344

(22) Filed: Nov. 18, 2016

(65) Prior Publication Data

US 2017/0136240 A1    May 18, 2017

Related U.S. Application Data

(60) Provisional application No. 62/257,039, filed on Nov. 18, 2015.

(51) Int. Cl.
| | |
|---|---|
| *A61N 1/00* | (2006.01) |
| *A61N 1/36* | (2006.01) |
| *A61N 1/05* | (2006.01) |
| *A61B 5/00* | (2006.01) |
| *A61B 5/04* | (2006.01) |
| *A61B 5/0476* | (2006.01) |

(52) U.S. Cl.
CPC ...... *A61N 1/36064* (2013.01); *A61B 5/04012* (2013.01); *A61B 5/4094* (2013.01); *A61B 5/4836* (2013.01); *A61N 1/0534* (2013.01); *A61N 1/36135* (2013.01); *A61N 1/36171* (2013.01); *A61B 5/0476* (2013.01)

(58) Field of Classification Search
CPC .............. A61N 1/36064; A61N 1/0534; A61N 1/36135; A61N 1/36171; A61N 1/0529; A61N 1/0539; A61N 1/0531; A61B 5/4094; A61B 5/4836
See application file for complete search history.

(56) References Cited

U.S. PATENT DOCUMENTS

| | | |
|---|---|---|
| 6,597,954 B1 | 7/2003 | Pless et al. |
| 8,374,696 B2 | 2/2013 | Sanchez et al. |
| 2007/0213786 A1* | 9/2007 | Sackellares .......... A61B 5/0476 607/45 |
| 2010/0121215 A1* | 5/2010 | Giftakis ................. A61B 5/031 600/544 |
| 2012/0277820 A1* | 11/2012 | Wu .................... A61N 1/36067 607/45 |

* cited by examiner

*Primary Examiner* — Mallika D Fairchild
(74) *Attorney, Agent, or Firm* — Pauley Erickson & Kottis

(57) ABSTRACT

A method and apparatus for preventing or terminating seizures, by stimulating a brain with at least two implanted electrodes, each implanted in a different one of at least two regions of the brain, with a frequency to emulate and/or disrupt neuronal synchrony. Upon detecting a potential or actual seizure occurrence, the frequency is electrically applied to the brain upon the detection to preempt or terminate the potential or actual seizure occurrence.

20 Claims, 9 Drawing Sheets

METHOD AND APPARATUS FOR PREVENTING OR TERMINATING EPILEPTIC SEIZURES

CROSS REFERENCE TO RELATED APPLICATION

This application claims the benefit of U.S. Provisional Patent Application Ser. No. 62/257,039, filed on 18 Nov. 2015. The Provisional Application is hereby incorporated by reference herein in its entirety and is made a part hereof, including but not limited to those portions which specifically appear hereinafter.

FIELD OF THE INVENTION

This invention relates generally to a method and apparatus for preventing or terminating seizures and, more particularly, to closed-loop stimulation protocols for preventing or terminating epileptic seizures.

BACKGROUND OF THE INVENTION

Epilepsy is a brain disorder characterized by recurrent and spontaneous derangements of normal brain activity. More than 50 million people worldwide have epilepsy. Approximately 70% of patients with epilepsy can be successfully treated with anti-epileptic drugs (AEDs). For these cases of intractable epilepsy with seizures either resistant to drug treatment or unsuitable for surgery, alternative therapeutic approaches are needed.

Electrical stimulation has been explored as a potential for benefit in treating epilepsy. With varying degrees of success, several studies have examined the effects of continuous and periodic stimulation for controlling seizures. Results from studies of the NeuroPacer™ Responsive Neurostimulator System (RNS) and the stimulation of the anterior nuclei of thalamus for epilepsy (SANTE) demonstrate that deep brain electrical stimulation (DBS) can reduce the occurrence of seizures in select patient populations. In the RNS study, approximately 54% of the patients implanted with the device experience greater than 50% reduction in seizure frequency from pre-implantation period. Most stimulation paradigms in therapeutic devices seek to reduce the frequency of seizure onset but are not specifically tailored to terminate a seizure once ictal activity has initiated simply because past efforts at this goal have not yet shown strong efficacy. Most researchers derive stimulation parameters by trial and error and frequently use as a starting point the experience of DBS for treating movement disorders. There is a continuing need for a stimulation protocol to improve the effectiveness of DBS in stopping epileptic seizures.

SUMMARY OF THE INVENTION

The invention provides a method and apparatus for preventing or terminating seizures with a stimulation frequency. In embodiments of this invention, the frequency emulates and/or disrupts neuronal synchrony that causes or at least occurs during seizures. The synchrony dynamics of a patient are observed as seizures naturally terminate and are used as an individualized, endogenous mechanism in a method and device for seizure preemption or termination by deep brain stimulation before or during a seizure. In some embodiments, the method includes stimulating a brain with a seizure termination frequency determined from and for a patient at two or more implanted brain electrodes, each implanted in a different one of two or more regions of the brain.

The invention further includes an apparatus for automatically preventing or terminating seizures. The apparatus includes a neurostimulator with a power supply connected to a stimulation generator that generates electrical stimulation through at least two electrodes for implanting in a patient's brain. The apparatus further includes a control protocol on a non-transitory recordable medium in executable combination with the stimulation generator and adapted to automatically stimulate at least two regions of the brain with a frequency to mimic and disrupt neuronal synchrony.

The invention further includes a non-transitory computer readable storage medium storing code executable by a processor/controller on an implantable neurostimulator or similar device to perform the method according to this invention. The code can be stored and execute on existing commercial devices or on a new device according to this invention.

In the example embodiments of this invention, multi-site brain dynamics within the circuit of Papez were calculated in a freely-moving chronic rat limbic epilepsy model induced via lithium chloride (LiCl)/pilocarpine i.p injections. Using empirical mode decomposition and coherence analysis, key dynamics were identified as seizures progressed. Synchrony dynamics seen as a seizure naturally terminated were reproduced using exogenous multi-site synchronized stimulation in an effort to stop a progressing seizure. Significantly improved efficacy of the stimulation at terminating seizures was found when the stimulation frequency and location of multi-site synchronized stimulation matched the endogenous synchrony dynamics observed during natural termination in the animal.

DESCRIPTION OF THE INVENTION

Figure 1:
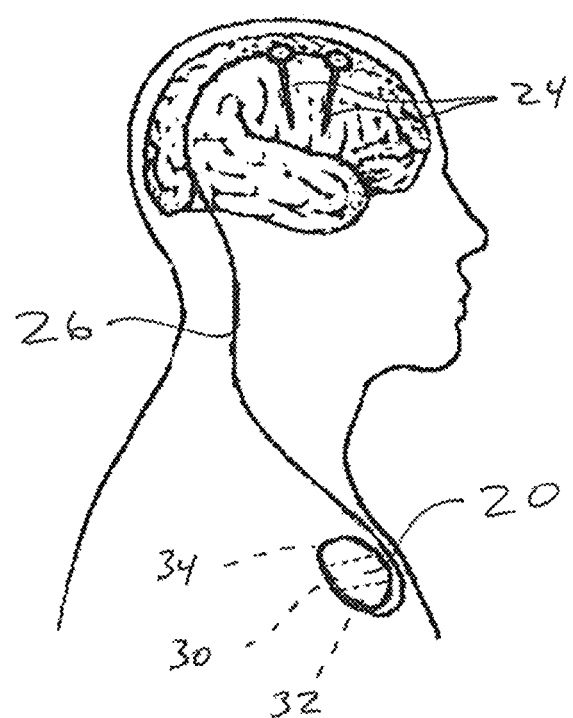
FIG. 1 generally illustrates an implanted apparatus according to one embodiment of this invention.

A general object of the invention is to use endogenous multisite brain dynamics to engineer effective closed-loop stimulation protocols for automatically preventing or terminating epileptic seizures. The invention involves stimulating a brain with at least two implanted electrodes, each implanted in a different one of at least two regions of the brain, with a frequency to disrupt neuronal synchrony. This invention includes a method and algorithm for providing deep brain electrical stimulation that are based on real-time brain activity of individuals with chronic recurrent seizures that are emblematic of epilepsy. The method of this invention is desirably implemented, without limitation, in a medical device that would be implanted in a human with chronic epilepsy to automatically carry out the detecting and preventing/terminating of a seizure event.

The invention includes a method that prevents and/or terminates seizures by determining and continually, automatically monitoring for occurrences of neuronal synchrony or other seizure indicator in regions of the patient's brain. Such synchrony has been found to precede and/or otherwise occur during a seizure event. The implanted electrodes can be used to identify synchronization and seizure between two or more regions of the brain during a seizure. In embodiments of this invention, frequencies of the seizure for the patient are measured and analyzed to determine a seizure termination frequency. The seizure termination frequency is determined from seizure frequencies measured across a seizure occurrence in the at least two regions of the brain. In preferred embodiments of this invention, the seizure termination frequency is obtained from electrophysiological dynamics of the brain measured at or near an end of a seizure within the brain. In this way, seizure dynamics (e.g., neuron frequencies and/or synchrony locations) can be determined for each individual patient. Once an appropriate frequency is determined for a patient, the frequency is electrically applied to the appropriate regions of the brain upon the detection of a potential or actual further seizure event to prevent or terminate the seizure. The frequency disrupts an evolving synchronization between structures in the at least two regions of the brain to preempt or otherwise terminate a seizure.

There are two disease-related pathological events that could be targeted with this new stimulation process. One would be stimulation to terminate a seizure. That is to say, the stimulation strategy of embodiments this invention would be activated once a seizure has been detected and then stimulation would be applied using the specific stimulation protocol tailored to an individual epilepsy patient that would apply multi-site stimulation to stop the seizure from continuing. The second event would be to prevent brain electrophysiological behavior from progressing to a full-blown seizure. Embodiments of the invention utilize key brain electrophysiological dynamics that arise just as full-blown seizures occur. In a similar strategy to termination, stimulation is applied to stop those dynamics from progressing by disrupting an evolving synchronization between structures in the brain tailored to a patient's individual brain electrical dynamics as seizures evolve.

FIG. 1 shows an implanted apparatus 20 according to one embodiment of this invention. The apparatus includes a neurostimulator 22 that is implanted in the patient's chest cavity. The neurostimulator 22 includes an internal power supply 30 to power a hardware/software based stimulation generator 32 to automatically generate electrical stimulation through two electrodes 24 connects by wires 26 disposed under the skin. The two electrodes are implanted within the brain; in two separate regions of the brain, such as, without limitation, each disposed in a different hemisphere of the brain.

The invention desirable has at least two electrodes, but preferably can include more than two electrodes, each in a different region of the brain. The use of three, four, six, eight, etc. electrodes can increase the ability to automatically determine synchronization events between two or more regions of the brain, thereby increasing the efficiency and/or effectiveness of the invention. Suitable electrodes, such as with sensor features for measuring and monitoring brain frequencies, are commercially available.

The apparatus 20 further includes a control protocol on a non-transitory recordable medium, such as within the neurostimulator 22, and in executable combination with the stimulation generator. The control protocol includes coded instructions to operate the electrodes and stimulate the two (or more) regions of the brain with a frequency to disrupt neuronal synchrony. The frequency disrupts an evolving synchronization between structures in the two regions of the brain to preempt or terminate a seizure. The frequency is synchronized to a predetermined seizure termination frequency of the at least two regions of the brain.

The apparatus 20 of embodiments of this invention further includes a detector 34 adapted to determine any occurring neuronal synchrony, and in doing so determines a potential or actual seizure occurrence. The detector can be hardware and/or coded instructions within the neurotransmitter 20 in combination with a sensor functionality of the electrodes 24. In embodiments of this invention, the detector 34 and electrodes 24 are used to monitor patient seizures and determine a predetermined seizure termination frequency for use in preempting or terminating future seizures according to this invention. In embodiments of this invention, the predetermined seizure termination frequency is obtained from electrophysiological dynamics of the brain measured at or near an end of a seizure within the brain.

There are currently two medical devices—one on the market and the other being clinically tested—that are implanted in humans with epilepsy that apply electrical stimulation to the brain in order to try to reduce seizure frequency. These devices (i.e., The Neuropace RNS™ system and the Medtronic SANTE™ device, respectively) do not use brain electrical dynamics to formulate stimulation protocols. In contrast, the invention described herein uses brain electrical dynamics tailored to individual patient brain dynamics as seizures evolve to fashion much more targeted stimulation protocols directed at pathological endogenous electrical activity in the brain. The method of this invention can be implemented on these known devices by loading the devices with the suitable software instructions.

Embodiments of this invention for treating epilepsy with deep brain stimulation (DBS) apply electrical stimulation in predetermined protocols (i.e., the timing of stimulation, the frequency, duration and location of stimulation) that are largely independent of the electrophysiological behavior occurring within the brain. The focus of the stimulation paradigm incorporated in this invention has been to apply excitatory stimulation with the goal of disrupting the evolution of onset of a seizure in a largely unspecified way. The invention uses analytical techniques to find endogenous synchronization dynamics related to seizures to formulate new deep-brain stimulation protocols to treat seizures. This new process has identified critical synchronization events in the brain that inform how to tailor stimulation to interfere with seizure evolution.

DBS is a potentially potent means for disrupting the aberrant rhythms that arise during a seizure. However, current DBS strategies typically employed are formulated a priori and do not reflect dynamics within the brain during ictogenesis which may severely limit stimulation efficacy. According to embodiments of this invention, DBS can be improved using endogenous dynamics to inform stimulation protocols. As discussed below, multi-site brain dynamics within the circuit of Papez was calculated in a chronic rat limbic epilepsy model. Stimulation/recording electrodes were placed in the CA3 region of both hippocampi and in the anteromedial nucleus of the thalamus. Deconvolution of signals using empirical mode decomposition and coherence analysis was used to identify key dynamics as seizures progressed. Synchronization of field potentials across sites occurred as both spontaneous and evoked seizures naturally terminated. The location and frequency of synchrony varied between subjects suggesting that endogenous rhythms during natural seizure termination may vary in humans as well. DBS efficacy was significantly more effective at stopping seizures when the frequency of multisite synchronized stimulation reflected endogenous synchrony dynamics observed in each subject. Thus, tailoring DBS protocols to individual endogenous rhythms that may represent how brains naturally resolve epileptic seizures can play a critical role in improving overall efficacy of this potentially important therapy.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Example I

Experiments were performed on male Sprague-Dawley rats.

Experimental protocols were conducted in accordance with National Institute of Health instructions for the care and use of laboratory animals. The rats had unlimited access to food and water. They were maintained in individual cages with 12-h light/dark cycles, with the light on from 6 AM-6 PM.

Surgery Procedures and Seizure Induction

Rats were anesthetized with a mixture of Ketamine (80 mg/kg) and Xylazine (10 mg/kg) delivered intra-peritoneally and then fixed within a stereotaxic apparatus (KOPF Model 900, CA, USA). The plane of anesthesia was continually assessed by reaction to a toe-pinch stimulus and corneal eye-blink reflex. Anesthesia was maintained with boosters containing Ketamine (20 mg/kg) delivered intramuscularly. A midline incision was made from the bridge of the nose to the posterior end of the cranium. Stereotaxic targets were calculated using a stereotaxic rat brain atlas. Lambda, Bregma and Sagittal sutures were used as landmarks to navigate to the desired stereotaxic points. The skull was perforated using a high speed stereotaxic drill (Micromotor Drill, Stoelting Co, Ill. USA) with 1.2-2 mm diameter drill tips. Six small burr holes were drilled: three were for the positioning of anchor screws and three for the placement of electrodes. Bipolar stainless steel electrodes (E363-1-2TW-SPC; Plastics One, Roanoke, Va., USA) were implanted into the CA3 regions of the bilateral hippocampi (−3.5 mm bregma, ±2.8 mm lateral, 3.7 mm deep) and the left anteromedial thalamus (−1.56 mm bregma, 1.0 mm lateral, 6.2 mm deep). The electrode sockets were inserted into a six-channel electrode pedestal (MS363; Plastics One) and the whole assembly was fixed to the skull using acrylic dental cement. After the cement dried (several minutes), the scalp was sutured closed and an electrode dust cap was screwed onto the pedestal. A week after surgery, the rats underwent seizure induction. Lithium chloride (127 mg/kg, i.p.) was injected 19-24 hours prior to pilocarpine administration. Scopolamine (1 mg/kg, i.p.) was administered 30 minutes before pilocarpine administration. Repeated doses (≤3) of pilocarpine (10 mg/kg, i.p.) were given to the rat every 30 minutes until the emergence of the first stage 4/5 seizure. Diazepam (10 mg/kg, i.p.) was injected 90 minutes after the onset of status epilepticus to quench ictal activity.

Stimulation and EEG Acquisition

A few weeks after seizure induction, local field potentials (LFPs) were recorded with an amplification per channel of 5000 and bandpass filtered (1-1000 Hz) using a Grass amplifier (QP511; Grass Technologies, West Warwick, R.I.). The signals were digitized at 2000 samples/second with a 32-bit A/D converter using an ADwin-light-16 unit (Jager GmbH, Lorsch, Germany). Spontaneous and evoked seizures were recorded from the animals. Seizures were evoked using 200 Hz square pulses (biphasic, 1 ms pulse width, and 80 µA) that lasted for 10 seconds. Software developed in-laboratory that employed Visual C# (Microsoft Corp., Seattle, Wash.) and MATLAB (The Mathworks, Inc, Natick, Mass.) compilers was used to acquire and analyze electrophysiological data. Therapeutic DBS was delivered by an electrical stimulator (WPI A359, Sarasota, Fla., USA). Square pulses of varying frequencies (biphasic, 1 ms pulse width, and 80 µA) were tested for their effectiveness in terminating the evoked seizures. For all subjects, video recordings were continuously maintained during all experimental protocols to provide behavioral correlates to electrographic activity.

Electrographic Analysis

LFPs from the bilateral hippocampii and the anteromedial nucleus of thalamus were decomposed into a series of intrinsic mode functions (IMFs) using the method of empirical mode decomposition (EMD). The instantaneous phase of each IMF was calculated using the Hilbert analytic signal method. The IMFs were clustered using eigenvalue-eigenvector clustering. Phase synchronization of the topmost cluster for each analysis window was assessed using the phase locking value. The significance of the observed phase synchrony was evaluated using surrogates and the frequencies of the IMFs that showed significant phase locking were estimated from their phase information. A more detailed explanation of this process can be found in T. Sobayo, et al., "Synchrony Dynamics Across Brain Structures In Limbic Epilepsy Vary Between Initiation And Termination Phases Of Seizures," *IEEE Trans Biomed Eng*, 2013; 60:821-829, herein incorporated by reference.

Synchrony Dynamics Observed in Spontaneous and Evoked Seizures

Figure 2:
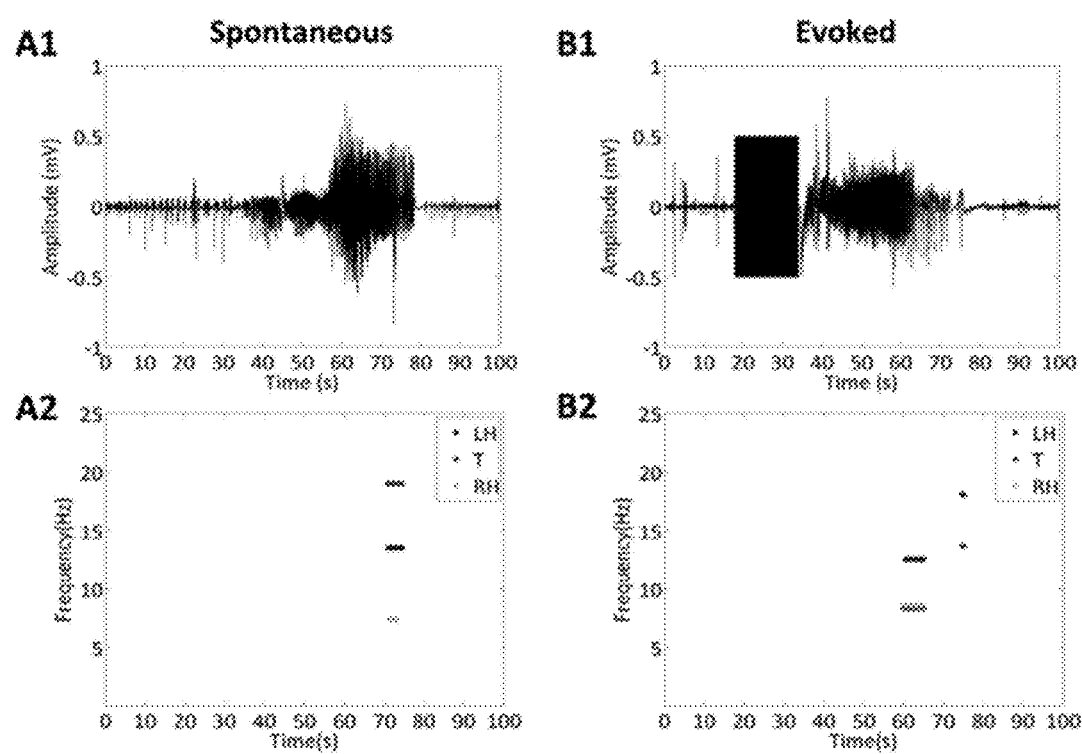
FIG. 2 shows that synchrony dynamics of oscillators in different structures in a rat brain during natural termination are similar between spontaneous and evoked seizures.
Figure 3:
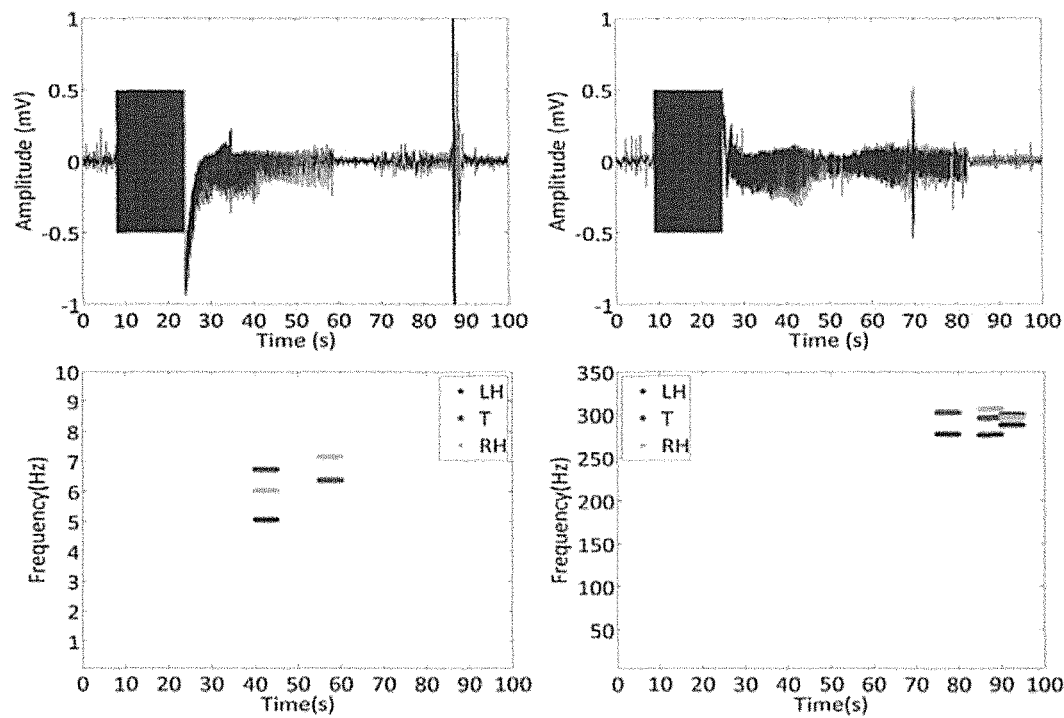
FIG. 3 shows that synchrony dynamics of oscillators during natural seizure termination in the rat brain varies from subject to subject.

LFPs were recorded in awake, free-moving rats from three locations implicated in limbic seizures as described above. Deconvolutions of the signals using empirical mode decomposition and coherence analysis were used to identify endogenous synchrony dynamics. FIG. 2 displays the LFP during either a spontaneous (panel A; left) or an evoked (panel B; right) seizure recorded from the same experimental animal. Panels A1 and B1 show 100 seconds of electrographic activity recorded from the intracranial electrode located in the CA3 region of the right hippocampus. Panels A2 and B2 show the corresponding synchrony analysis depicting the frequencies of the phase locked oscillators from the three recording sites. Note that the frequency of synchronization during natural seizure termination was similar for both spontaneous and evoked seizures. This result was common indicating the mode of seizure induction did not alter the observed synchrony at seizure termination. Evoked seizures and synchrony analysis for two other experimental animals is shown in FIG. 3. In the three animals shown, a period of synchronous locking of oscillators was seen at some or all of the three recording locations as the seizures terminated. However, the location and frequency of the synchrony varied between the animals. Since the epileptogenic induction protocols for these chronic animals were always the same, it indicates some heterogeneity in the seizure induction network. This difference may also reflect potential differences in seizure dynamics in human patients that may at least partly underlie differential efficacy to simple DBS protocols between patients. Hence, DBS protocols were tailored to individual subject synchrony dynamics and then tested to assess their efficacy in stopping evoked seizures in each subject.

Frequency of Multisite Synchronized Stimulation Affects the Efficacy of DBS

Figure 4:
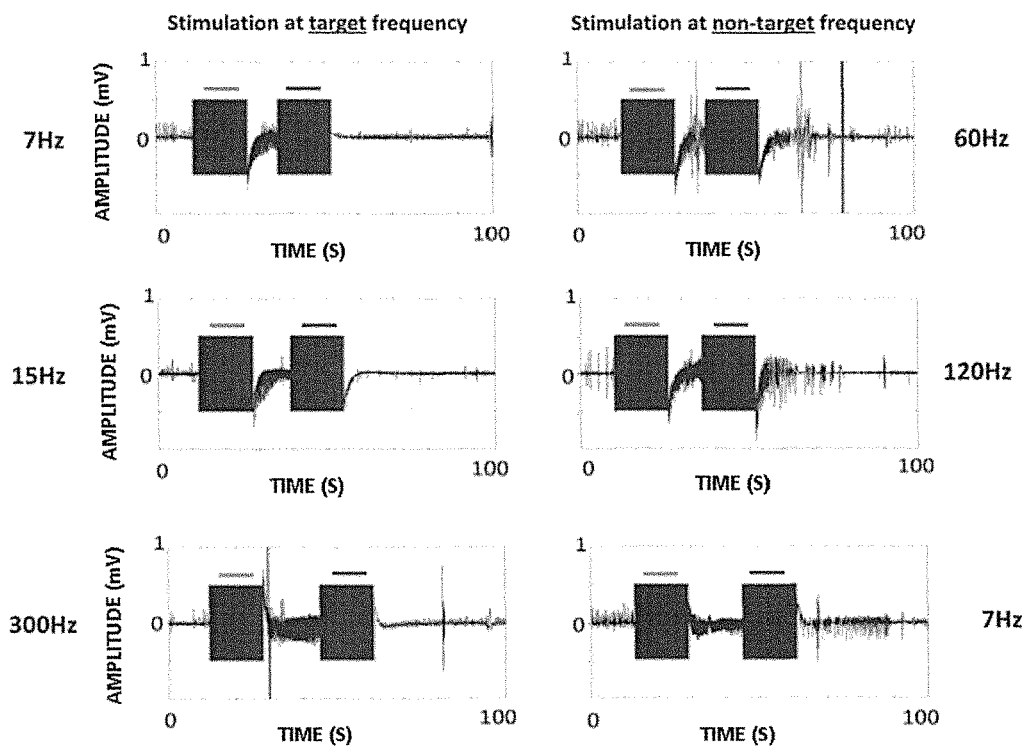
FIG. 4 shows therapeutic stimulation at the target frequency observed by synchrony analysis terminates evoked seizures faster than stimulation at non-target frequencies.

Seizures were evoked in each experimental subject as described above. The parameters for the DBS protocols were the same (i.e., pulse width, amplitude, duty cycle) except for the location and frequency of stimulation. For each animal, the frequency of the stimulation was chosen to be either the target frequency observed by the synchrony analysis to occur at natural termination or a frequency different from the target frequency. FIG. 4 displays 100 seconds of electrographic activity containing evoked seizures recorded from the intracranial electrode located in the CA3 region of the right hippocampus from three different rats. In each case, the left panels show therapeutic stimulation at the target frequency that matched the synchrony at natural termination for that animal. The right panels show therapeutic stimulation at frequencies other than the target frequencies. Stimulation at the frequencies reflecting the endogenous synchrony dynamics observed in each subject rapidly reset the LFP waveform back to its preictal state while stimulation at other frequencies did not appear to terminate the seizures since ictal activity continued for up to a minute after the therapeutic stimulation ended.

The effectiveness of terminating evoked seizures in the animals was measured using two criteria: (a) the time it took for the seizure to end after therapeutic stimulation was halted, and (b) an efficacy measure which took into account both the time it took for the seizure to stop after stimulation and the delay between the induction and therapeutic stimulation protocols. The target frequencies stop the seizures significantly faster than the control frequencies in most cases. It is interesting to note that in all three animals, the target frequencies stop the seizures significantly faster than the stimulation at 120 Hz (which is in a frequency range commonly used in stimulation experiments in rats). For the target frequencies, the time it took for seizures to stop were $14.70 \pm 3.41$ s, $12.71 \pm 3.25$ s, and $6.36 \pm 3.04$ s for rat 1, 2, and 3 respectively; while the times for stimulation at 120 Hz were $43.83 \pm 7.35$ s, $22.17 \pm 3.11$ s, and $20.29 \pm 4.09$ s for rat 1, 2, and 3 respectively ($p=0.002$, $p=0.04$, $p=0.007$). Stimulation efficacy measure also showed a similar trend where the target frequencies were more effective than the non-target frequencies.

Conclusion

The goal of this research was to investigate whether reproducing endogenous synchrony dynamics observed during natural seizure termination through exogenous electrical stimulation improved the efficacy of reverting epileptic seizures with DBS. The key findings of this study were: (1) the efficacy in reverting seizures via DBS was significantly improved when the stimulation frequency matched the target frequency obtained from synchrony analysis, and (2) the efficacy in reverting seizures was significantly improved when the multisite stimulation locations match the ones where endogenous synchrony emerged as seizures terminated.

Most studies in the use of DBS for epilepsy treatment derived stimulation parameters by trial and error. When it comes to the stimulation frequency, there exists competing rationale for selecting low, medium, or high. This might explain the varying degrees of success shown in several studies of using DBS to treat recurrent seizures. Since the endogenous dynamics of the seizures were not typically considered in the selection of the DBS frequency, differences in endogenous dynamics between subjects may lead to significantly different efficacy assessments of a single stimulation frequency. The data indicate that the time taken for a seizure to stop was significantly lower when the stimulation frequency matched that from the endogenous synchrony analysis of each subject. The target frequency for each subject varied significantly between subjects. For example, the 7 Hz frequency which was most effective in subject 1 was ineffective for subject 3. The location of the stimulation also appeared to be an important factor when it came to stimulation efficacy. For all three subjects, the hippocampus appears to be an important location for stimulation. Thalamic stimulation alone was less effective than bilateral hippocampal stimulation or a combination of both. The exact nature of the anti-convulsant action of electrical stimulation is not fully understood. Generally, accepted theories center around the following hypotheses: (a) preferential release of inhibitory neurotransmitters due to stimulation and/or (b) depolarization block, in which the stimulated neurons are inactivated because of stimulus-induced membrane hyperpolarization. It has also been suggested that stimulation with a high frequency has a lesion-like effect (depolarization block), while low frequency stimulation induces long-term depression (LTD) of stimulated neurons in the peri-electrode space. However, since the target frequencies in some cases were quite low (<20 Hz), it's unlikely that this depolarization block after 10 sec of therapeutic stimulation would have been significant.

Example II

Patterns of phase synchrony have been observed between three subcortical nuclei: bilateral hippocampi and the left anteromedial thalamus in the circuit of Papez only during the initiation and termination phases of seizures. This is consistent with other studies that looked at synchronization during experimental animal seizures as well as during termination in human seizures. In this study, multi-site brain dynamics within the circuit of Papez were calculated in a freely-moving chronic rat limbic epilepsy model. Using empirical mode decomposition and coherence analysis, key dynamics were identified as seizures progressed. Synchrony dynamics seen as a seizure naturally terminated were reproduced using exogenous multi-site synchronized stimulation in an effort to stop a progressing seizure. Significantly improved efficacy of the stimulation at terminating seizures was found when the stimulation frequency and location of multi-site synchronized stimulation matched the endogenous synchrony dynamics observed during natural termination in the animal.

This study investigated how the efficacy of DBS could be improved using endogenous dynamics to inform stimulation protocols. Multi-site brain dynamics within the circuit of Papez were calculated in a chronic rat limbic epilepsy model induced via LiCl/pilocaprine i.p. injections. Stimulation/recording electrodes were placed in the CA3 region of left and right hippocampi and the anteromedial nucleus of left thalamus. Deconvolution of local field potentials using empirical mode decomposition (EMD) and phase synchrony analysis revealed multisite coherence as seizures approached natural termination that could not be detected with Fourier analysis. Multisite stimulation used charge-neutral biphasic square waves at frequencies observed during naturally termination.

Synchronization of electrical activity across sites occurred as both spontaneous and evoked seizures naturally terminated. Further, the location and frequency of the synchrony varied between subjects but was stable in time within each animal. DBS efficacy was significantly more effective at rapidly stopping seizures when the frequency and location of multi-site stimulation reflected the endogenous synchrony dynamics observed in each subject as seizures naturally terminated.

These results strongly support the approach of tailoring DBS protocols to individual endogenous rhythms that may represent how brains naturally resolve epileptic seizures can significantly improve the overall efficacy of this potentially important therapy.

Material and Methods

Experiments were performed on male Sprague-Dawley rats. The experimental protocols were conducted in accordance with the National Institute of Health instructions for the care and use of laboratory animals. The rats had unlimited access to food and water. They were maintained in individual cages with 12-h light/dark cycles, with the light on from 6 AM to 6 PM. In nine rats, evoked and spontaneous seizures were collected and used in testing the efficacy of stimulation. Three out of the nine rats were removed from the study because the head caps became partially detached before completion of all experimental protocols.

Surgery Procedures and Seizure Induction

Rats (290-350 gm) were anesthetized with a mixture of Ketamine (80 mg/kg) and Xylazine (10 mg/kg) delivered intra-peritoneally and then fixed within a stereotaxic apparatus (KOPF Model 900, CA, USA). The plane of anesthesia was continually assessed by reaction to a toe-pinch stimulus and corneal eye-blink reflex. Anesthesia was maintained with boosters containing Ketamine (20 mg/kg) delivered intramuscularly. A midline incision was made from the bridge of the nose to the posterior end of the cranium. Stereotaxic targets were calculated using a stereotaxic rat brain atlas. Lambda, Bregma and Sagittal sutures were used as landmarks to navigate to the desired stereotaxic points. The skull was perforated using a high speed stereotaxic drill (Micromotor Drill, Stoelting Co, Ill. USA) with 1.2-2 mm diameter drill tips. Six small burr holes were drilled: three were for the positioning of anchor screws and three for the placement of electrodes. Bipolar stainless steel electrodes (E363-1-2TW-SPC; Plastics One, Roanoke, Va., USA) were implanted into the CA3 regions of the bilateral hippocampi (−3.5 mm bregma, ±2.8 mm lateral, 3.7 mm deep) and the left anteromedial thalamus (−1.56 mm bregma, 1.0 mm lateral, 6.2 mm deep). The electrode sockets were inserted into a 6 channel electrode pedestal (MS363; Plastics One) and the whole assembly was fixed to the skull using acrylic dental cement. After the cement dried (several minutes), the scalp was sutured closed and an electrode dust cap was screwed onto the pedestal.

One week after surgery, the rats underwent seizure induction. Lithium chloride (127 mg/kg, i.p.) was injected 19-24 hours prior to pilocarpine administration. Scopolamine (1 mg/kg, i.p.) was administered 30 minutes before pilocarpine administration. Repeated doses (≤3) of pilocarpine (10 mg/kg, i.p.) were given to the rat every 30 minutes until the emergence of the first stage 4/5 seizure. Diazepam (10 mg/kg, i.p.) was injected 90 minutes after the onset of status epilepticus to quench ictal activity.

Stimulation and EEG Acquisition

Spontaneous seizures typically arose 4-8 weeks after induction. Local field potentials (LFPs) were recorded with an amplification per channel of 5000 and bandpass filtered (1-1000 Hz) using a Grass amplifier (QP511; Grass Technologies, West Warwick, R.I.). The signals were digitized at 2000 samples/second with a 32-bit A/D converter using an ADwin-light-16 unit (Jäger GmbH, Lorsch, Germany). Spontaneous and evoked seizures were recorded from the animals. Seizures were evoked using 200 Hz square pulses (biphasic, 1 ms pulse width, and 80 µA) applied to the bilateral hippocampi that lasted for 10 seconds. Software developed in-laboratory which employed Visual C# (Microsoft Corp., Seattle, Wash.) and MATLAB (The Mathworks, Inc, Natick, Mass.) compilers was used to acquire and analyze electrophysiological data. Therapeutic DBS was delivered by an electrical stimulator (WPI A359, Sarasota, Fla., USA). Square pulses of varying frequencies (biphasic, 1 ms pulse width, and 80 µA) were tested for their effectiveness in terminating the evoked seizures. For all subjects, video recordings were continuously maintained during all experimental protocols to provide behavioral correlates to electrographic activity.

Electrographic Analysis

Local field potentials (LFPs) represent a sum of dendritic activity that may be inhibitory or excitatory; hence, these waveforms are necessarily multi-component. Since phase synchrony measures rely on prior extraction of the phase information from the time series, one critical step in synchrony analysis is phase determination. For a non-stationary signal, one method of extracting phase values instantaneously is the Hilbert analytic signal method for mono-component signals. Thus, a prior step to phase calculation will involve some form of filtering of the data. Almost all of the commonly employed decomposition algorithms assume something about the waveform shape or frequency bandwidth of interest a priori.

Empirical mode decomposition (EMD) allows one to filter a multi-component signal into a series of oscillators representing the (adaptively determined) characteristic time-scales of the individual components without a priori assumptions of linearity or stationarity. LFPs from the bilateral hippocampi and the anteromedial nucleus of thalamus were decomposed into a series of intrinsic mode functions (IMFs) using EMD. Instantaneous phase of each IMF was calculated using the Hilbert analytic signal method and the IMFs were clustered using eigenvalue-eigenvector clustering which provided a way of ranking different sets of synchronous oscillators. Phase synchronization of the topmost cluster for each analysis window was quantitatively assessed. The significance of the observed phase synchrony was evaluated using Fourier shuffled surrogates and the frequencies of the IMFs that showed significant phase locking were estimated from their phase information. A more detailed explanation of this process can be found in Blenkinsop et al., "The dynamic evolution of focal-onset epilepsies—combining theoretical and clinical observations," *Eur. J. Neurosci.* 2012; 36:2188-2200, and Fine et al., "Assessing instantaneous synchrony of nonlinear nonstationary oscillators in the brain," *J. Neurosci. Methods* 2010; 186:42-51.

The average frequency between oscillators from different locations that showed significant phase locking was used as the target frequency for therapeutic stimulation aimed at stopping ongoing pathological electrographic activity. Other frequencies (derived from the literature) and stimulation locations were used as controls to assess the comparative efficacies of the stimulation protocols at reverting epileptic seizures.

Efficacy of therapeutic stimulation (TS) was assessed with respect to the duration of a seizure relative to those that naturally resolved with no therapeutic stimulation (NS). This relationship is provided by:

$$\text{Efficacy}=1-A(1-e^{-1TS/1NS}),$$

where $A=1/1-e^{-1}$, such that when seizure duration following therapeutic stimulation is the same as with no such stimulation, Efficacy=0. Stimulation that immediately disrupted seizures have an Efficacy=1 and therapeutic stimulation that produced seizure durations longer than that of control (i.e., NS) produced negative efficacies.

Statistical Analysis

All data were presented as mean±standard error of the mean. SigmaStat (Systat Software Inc., USA) was employed for statistical analysis. One way ANOVA or Kruskal-Wallis one way ANOVA on ranks was used to determine the effectiveness of DBS protocols depending on conditions of normality. A value of $p<0.05$ was considered statistically significant.

Frequency of Multi-Site Synchronized Stimulation Affects the Efficacy of DBS

Figure 5:
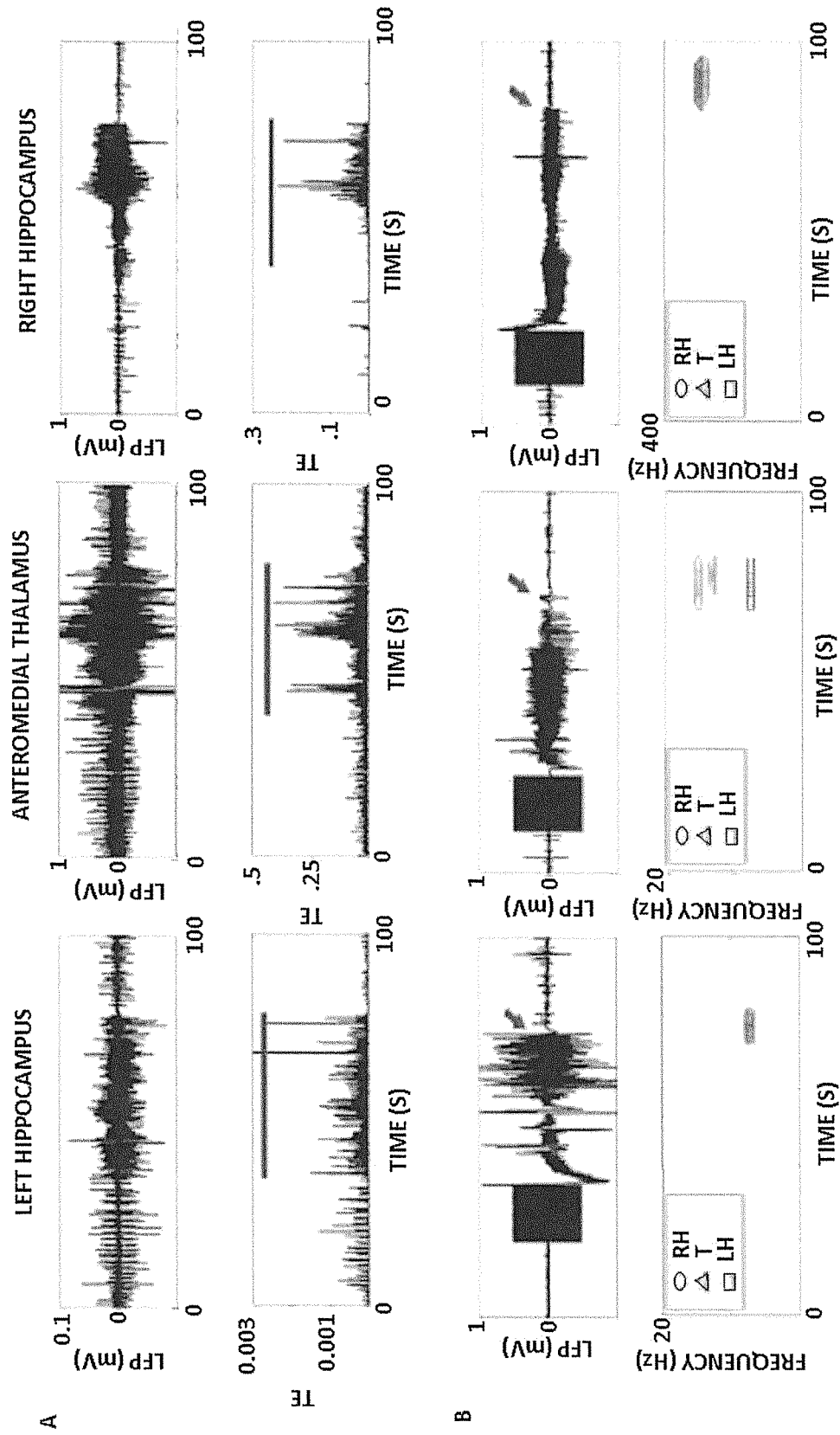
FIG. 5 shows endogenous synchrony dynamics within circuit of Papez during temporal lobe seizures.

Brain dynamics were calculated at three sites within the circuit of Papez in a chronic rat limbic epilepsy model. FIG. 5 displays local field potentials (LFPs) recorded in awake, freely-moving rats during a spontaneous seizure (panel A). Teager Energy (TE), which depends on both amplitude and frequency of a time series signal, was an excellent indicator of seizure onset and offset that correlated well with behavioral indicators of seizure-induced motor activity (Racine scale≥3). A threshold of the mean of the TE plus five times the standard deviation was used as criteria for indicating valid seizure activity. Panel B shows electrographic activity during evoked seizures recorded from the intracranial electrode location in the CA3 region of the right hippocampus in three different rats. In all three animals, periods of synchronous locking of oscillators at some or all of the three recording locations as seizures naturally terminated were found. This synchrony was only observed at or near the end of a seizure. The location and frequency of the synchrony varied between animals but was stable over time for each animal (measured up to 5 months post-induction). In nine animals, five different frequencies were observed at natural termination. These termination coherence frequencies were (numbers of animals in parentheses): 7 Hz (3), 15 Hz (2), 120 Hz (2), 250 Hz (1), and 300 Hz (1). Natural termination coherence frequencies were measured a minimum of 2 times for each animal.

Figure 6:
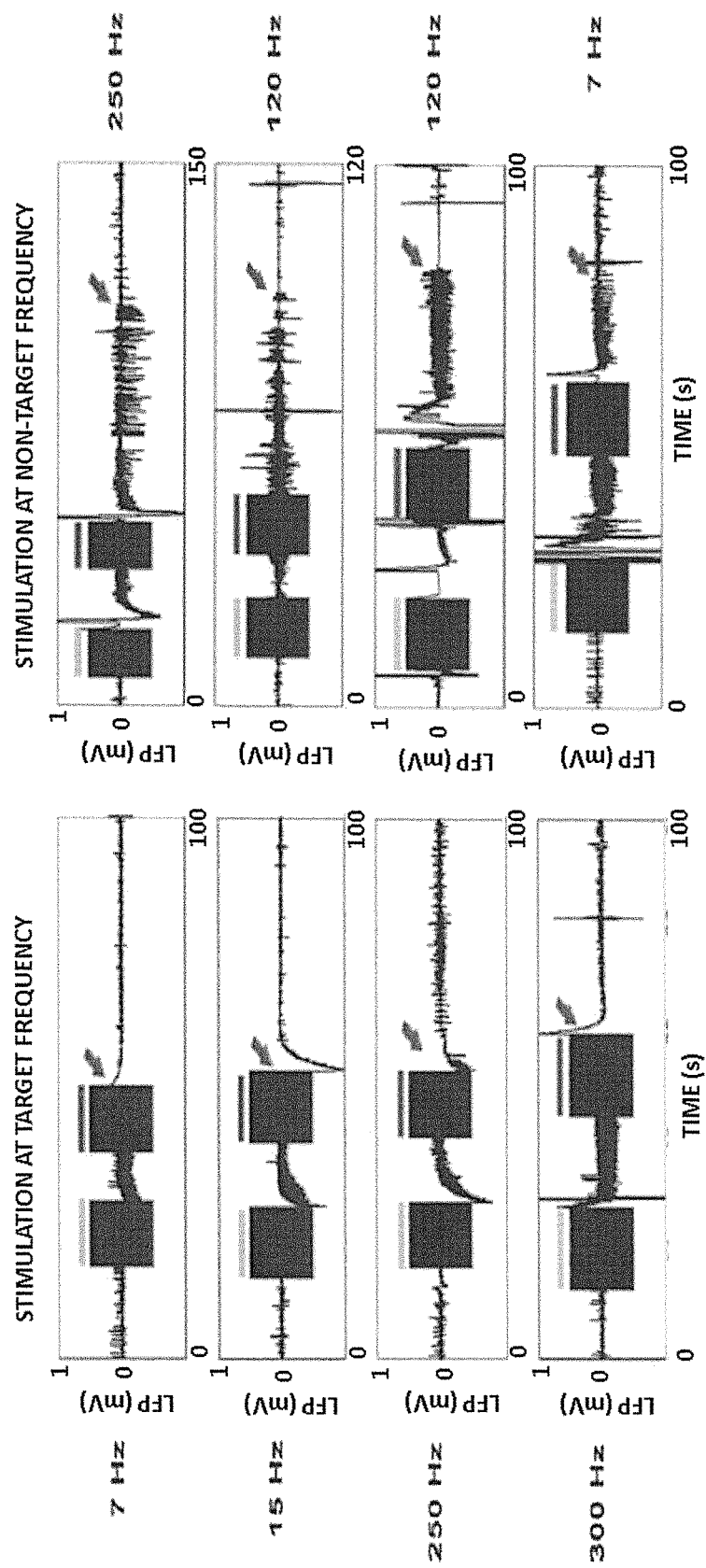
FIG. 6 displays electrographic activity containing evoked seizures recorded from the intracranial electrode located in the CA3 region of the right hippocampus from four rats.
Figure 7:
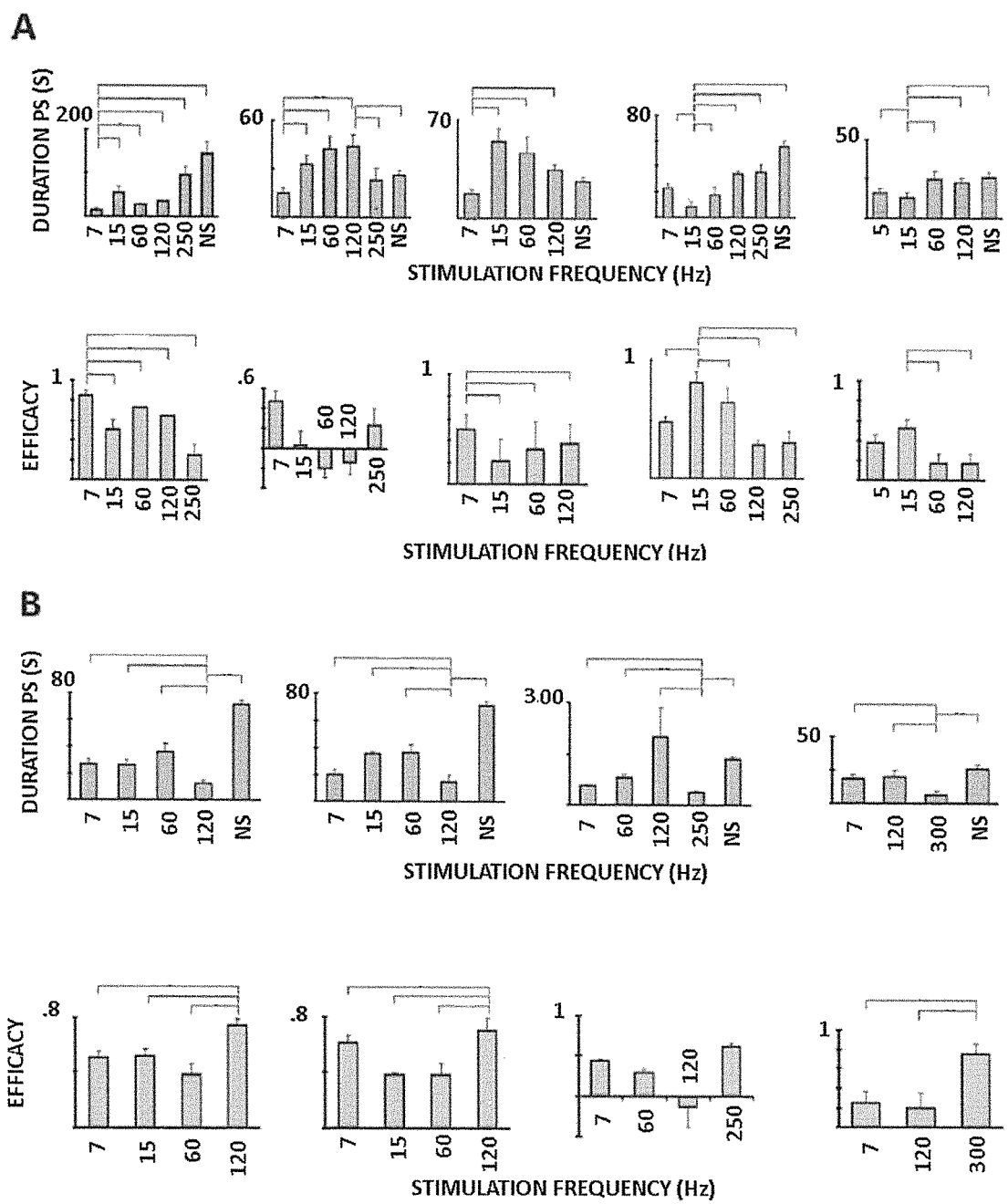
FIG. 7 summarizes responses to therapeutic DBS as a function of stimulation frequency during temporal lobe seizures.

FIG. 6 displays electrographic activity containing evoked seizures recorded from the intracranial electrode located in the CA3 region of the right hippocampus from four rats. In each case, the left panels show therapeutic stimulation at the target stimulation frequencies defined as the frequency of endogenous synchrony at natural seizure termination for that subject. The right panels show therapeutic stimulation at frequencies other than the target frequencies (non-target). Stimulation at the target frequency was significantly faster than non-target frequencies at terminating ongoing seizure activity. FIG. 7 shows the time it took seizures to stop at different stimulation frequencies (upper) and the relative efficacy of stimulation frequencies (lower) for nine different animals with either low target frequencies (panel A) or high target frequencies (panel B).

The effectiveness of terminating evoked seizures in the animals was measured using two criteria: (a) the time it took for the seizure to end after therapeutic stimulation was halted, and (b) an efficacy measure which assessed the duration of a seizure relative to those that naturally resolved with no therapeutic stimulation. The details of the latter measure can be found in the Methods section. Stimulating at the endogenous synchrony frequency observed at natural termination for that animal was significantly better at stopping an ongoing seizure than at other frequencies (p-values as shown in FIG. 7 for each subject). Note that for one of the animals with target frequencies 7 and 250 Hz each, stimulation at non-target frequencies actually produced negative efficacies indicative of stimulation that actually lengthened seizure duration beyond that observed without any therapeutic stimulation (NS).

Synchrony Dynamics Observed in Spontaneous and Evoked Seizures

Figure 8:
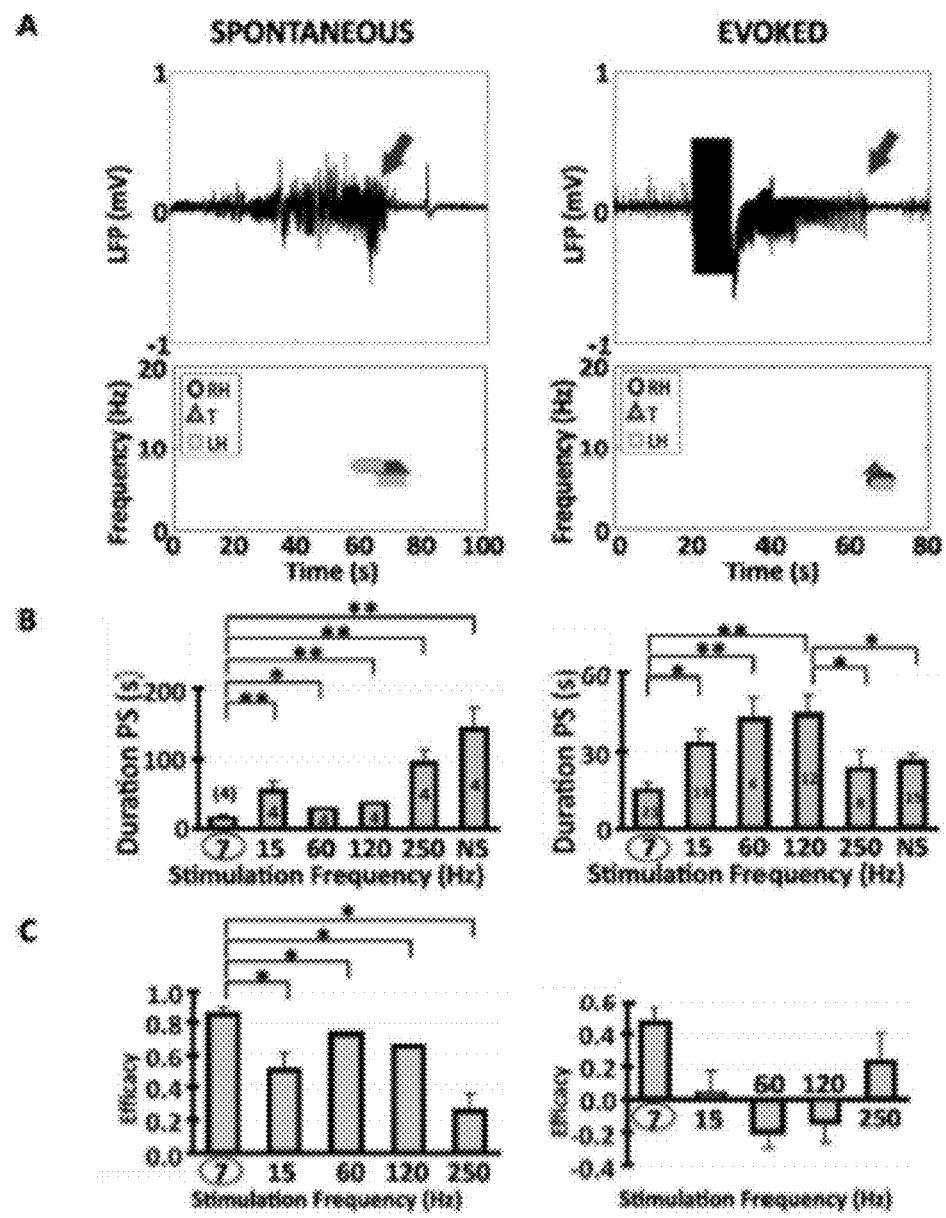
FIG. 8 shows that endogenous synchrony dynamics and frequency-sensitivity of therapeutic stimulation are similar in spontaneous vs. evoked seizures.

Because the rate of occurrence of spontaneous seizures could vary greatly between animals, seizures were often evoked by a 10 second induction stimulation in these experiments, as described above. The question arises as to whether synchrony dynamics at termination and/or the efficacy of the DBS protocols differed between spontaneous vs. evoked seizures. In fact, analysis comparing both the dynamic of synchrony at natural termination and the dependence of the efficacy of therapeutic DBS (FIG. 8) within subjects indicated that the termination dynamics were largely independent of the mechanism of seizure induction suggesting that the synchrony at natural termination was a function of the underlying network within the brain rather than the mechanism of seizure onset ($p=0.004$ for spontaneous seizures and $p<0.001$ for evoked seizures). The significantly better efficacy of stimulation at the natural termination frequency was observed in both induction models. Note that nontarget stimulation protocols in the evoked seizures produced negative efficacies indicating that nontarget stimulation frequencies actually lengthened seizure durations compared to controls.

Figure 9:
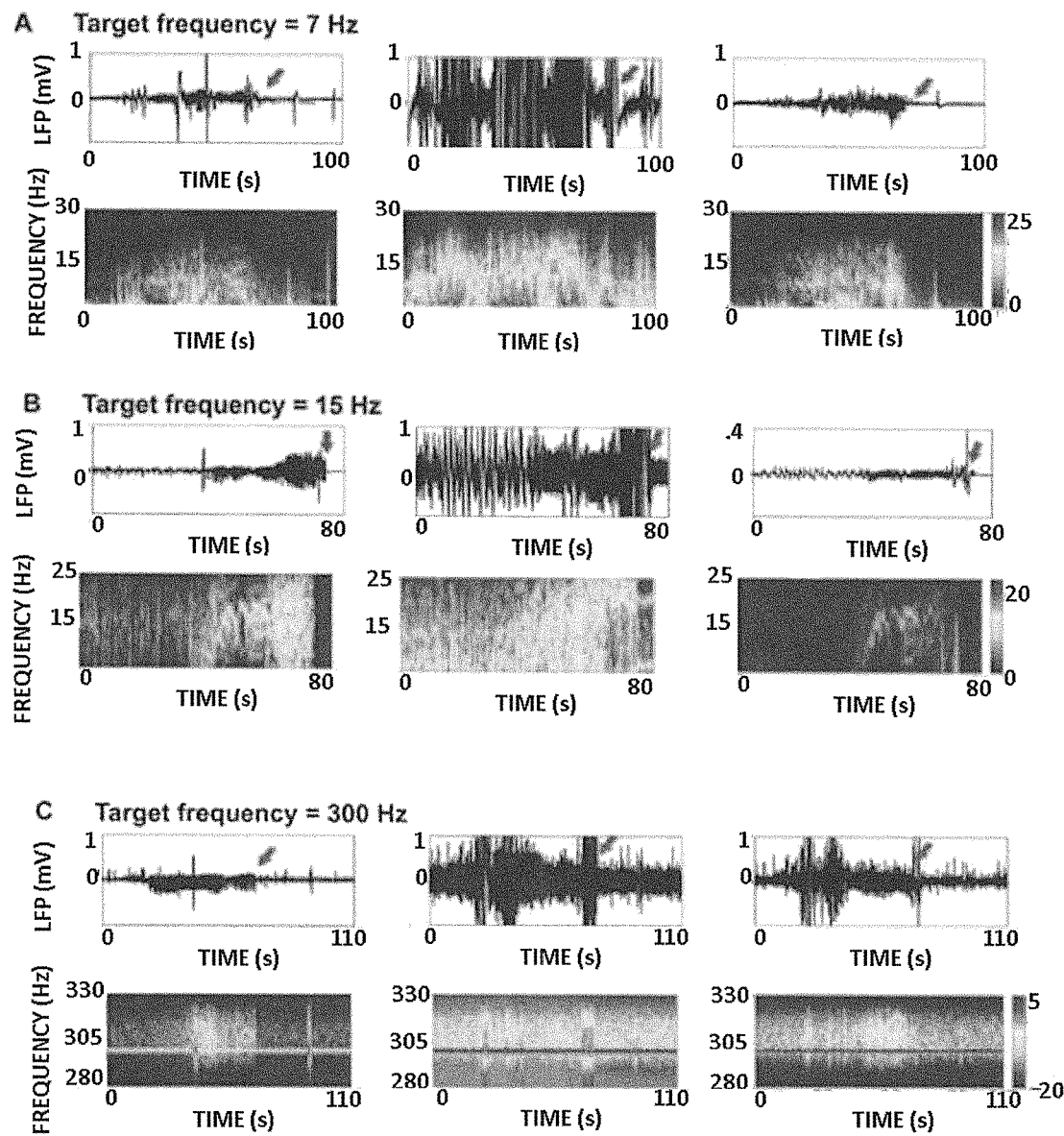
FIG. 9 is Fourier-derived spectrograms in rats with different endogenous termination dynamics.

Coherence analyses of the LFP signals at each of the three brain locations were conducted after signals were first decomposed using EMD. Because EMD neither assumes linearity nor stationarity of the underlying signals, the question arises as to whether the simpler and more common decomposition method available via Fourier analysis would have resulted in a similar finding. The size of the temporal window used in Fourier analysis depends, in part, on the critical frequency characteristics of the signal being analyzed—the lower the frequency components being analyzed, the longer the window required. Longer windows make brief but critical phase coherence difficult to detect. The analysis of nine epileptic rats using EMD detected brief (≥100 ms) but significant synchronies between 7 Hz and 300 Hz. Fourier spectrograms (FIG. 9) of seizures from three rats do show evidence of higher power components in the same coherent frequency range found with the primary analytical technique. But the spread of frequencies of the high amplitude oscillators using Fourier was over a much larger range relative to the target frequencies found with EMD reducing the likelihood of locating brief but significant oscillator synchrony, especially at the lower frequencies, and is likely to be insufficient to determine the critical stimulation parameters as provided by the methodology. Hence, because of the high sensitivity of DBS efficacy on mirroring endogenous rhythms, the use of this more common frequency deconvolution technique appears largely inadequate.

Location of Stimulation Affects the Efficacy of DBS

Figures 10, 11:
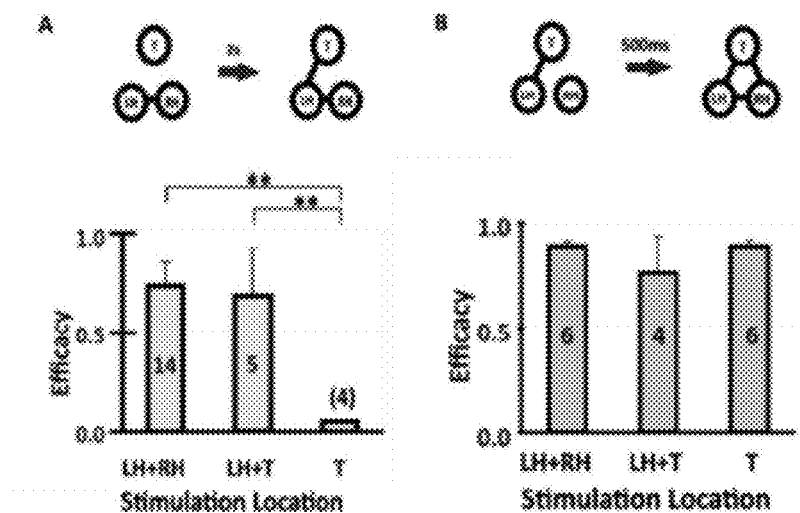
FIG. 10 shows that sensitivity of efficacy to DBS stimulation locations depends on where coherence at natural termination occurs.
FIG. 11 is a table showing the number of seizures that have undergone experimental protocols for each of nine animal subjects.

The analysis revealed multi-site dynamics that varied not only in the frequency observed at natural termination of seizures but also the locations of synchronous electrographic activity. FIG. 10 shows different synchrony patterns determined in two rats. When synchrony at natural termination was observed tightly only across the two hippocampi (panel A), stimulation at the target frequency was not effective (i.e., no better than with no therapeutic stimulation) when applied only to the anteromedial thalamus. However, when synchrony in a different subject rapidly occurred across all three structures (panel B), target frequency stimulation applied simultaneously to different variants of these three structures was found to be equally efficacious.

The goal of this research was to investigate whether reproducing endogenous synchrony dynamics observed during natural seizure termination through exogenous electrical stimulation improved the efficacy of reverting epileptic seizures with DBS. A total of 389 seizure events in nine different rat subjects was recorded in this study and tested for the efficacy of stimulation protocols based on endogenous rhythms (see Table, FIG. 11). The key findings of this study were: (1) the efficacy in reverting seizures via DBS was significantly improved when the stimulation frequency matched the target frequency obtained from synchrony analysis, and (2) the efficacy in reverting seizures with DBS greatly depended on matching the locations of multi-site stimulation to those brain regions displaying endogenous synchrony as seizures naturally terminated.

Most studies in the use of DBS for epilepsy treatment derive stimulation parameters by trial and error. When it comes to the stimulation frequency, there exists competing rationale for selecting low, medium, or high. This might explain the varying degrees of success shown in several studies of using DBS to treat recurrent seizures. Since the endogenous dynamics of the seizures were not typically considered in the selection of the DBS frequency, differences in endogenous dynamics between subjects may lead to significantly different efficacy assessments of a single stimulation frequency. The data indicate that the time taken for a seizure to stop was significantly lower when the stimulation frequency matched that from the endogenous synchrony analysis of each subject. The location of the stimulation also appeared to be an important factor when it came to stimulation efficacy. For all subjects, the hippocampus appeared to be an important location for stimulation. Thalamic stimulation alone was less effective than bilateral hippocampal stimulation or a combination of both. One or both hippocampi showed involvement in the synchrony that first emerged as seizures naturally terminated in all subjects. While there was significant difference in the time it took for a seizure to stop between purely hippocampal stimulation and purely thalamic stimulation, a significant difference between bilateral hippocampal stimulation and unilateral (left or right) hippocampal stimulation (p=0.290) was not detected. Because of the stronger commissural connections between both hippocampi in rats than in humans, this sensitivity to sites of stimulation may be even higher when stimulation is applied clinically to human epilepsy patients because of the lower connectivity and hence higher electrical isolation between hemispheres.

The exact nature of the anti-convulsant action of electrical stimulation is not fully understood. Generally accepted theories center around the following hypotheses: (a) preferential release of inhibitory neurotransmitters due to stimulation and/or (b) depolarization block, in which the stimulated neurons are inactivated because of stimulus-induced membrane hyperpolarization. It has also been suggested that stimulation with a high frequency has a lesion-like effect (depolarization block), while low frequency stimulation induces long-term depression (LTD) of stimulated neurons in the peri-electrode space. However, since the target frequencies in some cases were quite low (<201 Hz), it's unlikely that this depolarization block after 10 sec of therapeutic stimulation would have been significant.

Thus, the invention provides methods of treating seizures by applying individualized, closed-loop stimulation protocols for preventing or terminating epileptic seizures. The methods can be implemented by software implemented protocols on current commercial neurostimulators to determine appropriate synchrony locations and/or termination frequencies, and then automatically apply one or more appropriate frequencies upon detecting a further seizure event.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method of preventing or terminating seizures, comprising:
   determining neuronal synchrony between at least two sites of a brain of a patient;
   stimulating the brain with at least two implanted electrodes, each implanted in a different one of at least two regions of the brain, with a frequency to emulate or disrupt the neuronal synchrony, wherein the frequency comprises a predetermined seizure termination frequency determined from seizure frequencies measured across a seizure occurrence in the at least two regions of the brain.

2. The method of claim 1, wherein the stimulation comprises deep brain stimulation before or during a seizure.

3. The method of claim 1, wherein the frequency is synchronized to a predetermined seizure termination frequency of the at least two regions of the brain.

4. The method of claim 3, further comprising detecting a potential or actual seizure occurrence via the neuronal synchrony, wherein the frequency is electrically applied to the brain upon the detection of the potential or actual seizure occurrence.

5. The method of claim 1, wherein the frequency disrupts an evolving synchronization between structures in the at least two regions of the brain to preempt or terminate a seizure.

6. The method of claim 1, wherein the predetermined seizure termination frequency is obtained from electrophysiological dynamics of the brain measured at or near an end of a seizure within the brain.

7. The method of claim 6, wherein the electrophysiological dynamics comprise a termination frequency that is synchronized between the at least two regions of the brain at or near the end of the seizure within the brain.

8. The method of claim 1, wherein the electrodes are actuated by an implanted neurostimulator including a power source.

9. The method of claim 8, wherein the neurostimulator comprises a stimulation generator protocol on a non-transitory recordable medium and executable to stimulate the at least two regions of the brain with the frequency synchronized to the predetermined seizure termination frequency.

10. A non-transitory computer readable storage medium storing code executable on an implantable neurostimulator to perform the method according to claim 1.

11. The method of claim 1, further comprising determining the neuronal synchrony between more than two sites of the brain.

12. A method of preventing or terminating seizures, comprising:
    determining a neuronal synchrony frequency between at least two regions of a brain; and
    stimulating the brain with at least two implanted electrodes, each implanted in a different one of the at least two regions of the brain, to emulate or disrupt the neuronal synchrony by electrically applying the frequency to the brain upon the determining of the neuronal synchrony.

13. The method of claim 12, wherein the frequency comprises a predetermined seizure termination frequency determined from seizure frequencies measured across a seizure occurrence in the at least two regions of the brain.

14. An apparatus for preventing or terminating seizures, comprising:
    a neurostimulator including a stimulation generator and a power supply connected to the stimulation generator, wherein the stimulation generator generates electrical stimulation for and through at least two electrodes implantable within a brain; and
    a control protocol on a non-transitory recordable medium in executable combination with the stimulation generator and adapted to stimulate at least two regions of the brain with a frequency to emulate or disrupt neuronal synchrony, wherein the frequency disrupts an evolving synchronization between structures in the at least two regions of the brain to preempt or terminate a seizure, and the frequency comprises a predetermined seizure termination frequency predetermined from seizure frequencies measured across a seizure occurrence in the at least two regions of the brain.

15. The apparatus of claim 14, wherein the frequency is synchronized to a predetermined seizure termination frequency of the at least two regions of the brain.

16. The apparatus of claim 15, wherein the predetermined seizure termination frequency is determined by the neuro stimulator and electrodes.

17. The apparatus of claim 14, wherein the predetermined seizure termination frequency is obtained from electrophysiological dynamics of the brain measured at or near an end of a seizure within the brain.

18. An apparatus for preventing or terminating seizures, comprising:
    a neurostimulator including a stimulation generator and a power supply connected to the stimulation generator, wherein the stimulation generator generates electrical stimulation for and through at least two electrodes implantable within a brain;
    a control protocol on a non-transitory recordable medium in executable combination with the stimulation generator and adapted to stimulate at least two regions of the brain with a frequency to emulate or disrupt neuronal synchrony, wherein the frequency disrupts an evolving synchronization between structures in the at least two regions of the brain to preempt or terminate a seizure; and
    a detector adapted to determine the neuronal synchrony, wherein the frequency is electrically applied to the brain upon the determination of the neuronal synchrony.

19. The apparatus of claim 18, wherein the detector determines a potential or actual seizure occurrence, and the frequency is electrically applied to the brain upon the detection of the potential or actual seizure occurrence.

20. The apparatus of claim 18, wherein the frequency comprises a predetermined seizure termination frequency predetermined from seizure frequencies measured across a seizure occurrence in the at least two regions of the brain.

* * * * *